United States Patent [19]
Cassel et al.

[11] Patent Number: 5,750,808
[45] Date of Patent: May 12, 1998

[54] DEHYDROHALOGENATION PROCESSES

[75] Inventors: Wendell Richard Cassel, Newark, Del.; David Richard Corbin, West Chester, Pa.; V.N. Mallikarjuna Rao, Wilmington, Del.

[73] Assignee: E. I. du Pont de Nemours and Company, Wilmington, Del.

[21] Appl. No.: 677,063

[22] Filed: Jul. 9, 1996

[51] Int. Cl.$^6$ .................................................. C07C 17/00
[52] U.S. Cl. ........................ 570/157; 570/135; 570/136; 570/177
[58] Field of Search ........................ 570/157, 135, 570/136, 177

[56] References Cited

U.S. PATENT DOCUMENTS

| | | | |
|---|---|---|---|
| 2,404,374 | 7/1946 | Harmon | 260/648 |
| 4,605,798 | 8/1986 | Abel et al. | |
| 5,396,000 | 3/1995 | Nappa et al. | 570/157 X |

FOREIGN PATENT DOCUMENTS

| | | |
|---|---|---|
| 1152021 | 5/1969 | United Kingdom. |
| 2004539 | 8/1978 | United Kingdom. |
| 1578933 | 11/1980 | United Kingdom. |
| WO94/02440 | 2/1994 | WIPO. |

OTHER PUBLICATIONS

A.M.Lovelace et al., Aliphatic Flourine Compounds, *Am. Chem. Soc. Reinhold Publishing Corp.*, 100–104, 1958.
R.M.Barrer et al., Sorption and Reactivity of Simple Organic Molecules in Chabazite, *Trans. Faraday Soc.*, 49, 940–948, Mar. 1953.

*Primary Examiner*—Paul F. Shaver

[57] ABSTRACT

A process is disclosed for the dehydrohalogenation of partially halogenated ethanes of the formula $C_2H_aCl_bF_c$ where a is an integer from 1 to 4, b is an integer from 0 to 3 and c is an integer form 1 to 5 to produce olefins selected from the group consisting of $C_2H_{a-1}Cl_{b-1}F_c$ and $C_2H_{a-1}Cl_bF_{c-1}$. The process involves contacting $C_2H_aCl_bF_c$ with a zeolite selected from the group consisting of NaX and CsY. Selective reaction of one isomer from a mixture of two isomers is disclosed as a means for purification of the relatively unreactive isomer. Also disclosed is a process for producing perfluorocyclobutane which involves contacting $CHF_2CClF_2$ with such zeolites.

11 Claims, No Drawings

DEHYDROHALOGENATION PROCESSES

This application claims the priority benefit of U.S. Provisional Application 60/001,033, filed Jul. 11, 1995.

FIELD OF THE INVENTION

This invention relates to processes for the dehydrohalogenation of hydrochlorofluorocarbons and hydrofluorocarbons to produce fluoroolefins and more particularly to the use of zeolites for such processes.

BACKGROUND

Fluoroolefins are useful for the preparation of fluoroplastics, fluoroelastomers, rubber stabilizers and as monomers in the preparation of fluorinated copolymers. Fluoroolefins can be produced by a variety of methods. The olefins tetrafluoroethylene and hexafluoropropylene can be manufactured by the high temperature (typically greater than 600° C.) pyrolysis of chlorodifluoromethane. Vinylidene fluoride and vinyl fluoride can be prepared by pyrolysis of 1,1,1-trifluoroethane and 1,1-difluoroethane, respectively. Perfluorobutylethylene can be prepared by treatment of $C_4H_9CH_2CH_2I$ with sodium hydroxide. Chlorotrifluoroethylene can be prepared by treatment of $CCl_2FCClF_2$ with zinc. Because of the many uses for fluoroolefins, new methods of preparation are continually being sought.

Products containing isomers of $C_2H_2F_4$ and $C_2HClF_4$ are produced in various degrees of isomer purity. In the manufacture of $C_2Cl_2F_4$, where the $C_2Cl_2F_4$ isomers are often produced by the chlorofluorination of perchloroethylene the product typically consists of a mixture of the isomers, $CClF_2CClF_2$ (CFC-114) and $CF_3CCl_2F$ (CFC-114a). This is exemplified in U.S. Pat. No. 4,605,798. If the CFC-114s are then used to produce $CHF_2CClF_2$ (HCFC-124a), $CF_3CHClF$ (HCFC-124), $CHF_2CHF_2$ (HFC-134) or $CH_2FCF_3$ (HFC-134a) by hydrodehalogenation, the products often consist of a mixture of $C_2HClF_4$ and $C_2H_2F_2$ isomers (see e.g., GB 1,578,933).

A major use of the $C_2H_2F_4$ and $C_2HClF_4$ isomers is as refrigeration fluids for a number of applications.

It has been found that for many applications, the presence of the undesired isomer of an isomer pair can significantly alter the physical and chemical properties of the desired isomer. For example, variation in the HFC-134/HFC-134a ratio in the product results in dramatic variability in the thermodynamic properties critical for use in refrigeration applications. For use as a raw material feed, the presence of the unwanted isomer can result in yield loss due to increased side reactions. As a result, there have been continually increasing market and process demands for high isomer purity materials. Consequently, identification of methods of purification represents a significant aspect of preparing the compounds for specific applications.

The $C_2H_2F_4$ and $C_2HClF_4$ isomer pairs are close boiling with the following boiling points: HFC-134, −23° C. and HFC-134a, −26.5° C., HCFC-124, −12° C. and HCFC-124a, −10° C. Distillation is consequently largely ineffective as a means of separation.

SUMMARY OF THE INVENTION

This invention provides a process for the dehydrohalogenation of partially halogenated ethanes (i.e., hydrochlorofluorocarbons and/or hydrofluorocarbons) of the formula $C_2H_aCl_bF_c$ where a is an integer from 1 to 4, b is an integer from 0 to 3 and c is an integer form 1 to 5 to produce olefins selected from the group consisting of $C_2H_{a-1}Cl_{b-1}F_c$ and $C_2H_{a-1}Cl_bF_{c-1}$. This process comprises contacting $C_2H_aCl_bF_c$ with a zeolite selected from the group consisting of NaX and CsY. Selective reaction of one isomer from a mixture of two isomers is provided as a means for purification of the relatively unreactive isomer.

The invention also provides a process for producing perfluorocyclobutane. This process comprises contacting $CHF_2CClF_2$ with said zeolite.

DETAILS OF THE INVENTION

The invention is applicable to the dehydrohalogenation of two-carbon hydrochlorofluorocarbons and/or hydrofluorocarbons that contain one or more fluorine atoms in the molecule. Examples of compounds which may be dehydrohalogenated include $CHCl_2CClF_2$, $CHCl_2CF_3$, $CHF_2CClF_2$, $CHClFCF_3$, $CHCl_2CHF_2$, $CHF_2CHF_2$, $CH_2FCF_3$, $CH_3CClF_2$, $CH_3CF_3$ and $CH_3CHF_2$.

The reaction of particular compounds, including isomers, can be dependent upon the particular temperature employed. Thus, at a particular temperature some compounds may readily react while others may require higher temperatures to achieve comparable reaction rates. Of particular note is the selective reaction of $CHF_2CHF_2$ from a mixture of $CHF_2CHF_2$ and $CH_2FCF_3$ and the selective reaction of $CHF_2CClF_2$ from a mixture of $CHF_2CClF_2$ and $CHClFCF_3$. Accordingly, this invention provides a process for the preparation of highly pure $CH_2FCF_3$ from isomeric mixtures of $C_2H_2F_4$, comprising contacting the isomer mixture with said zeolite to produce a product mixture which contains $CHF=CF_2$ and $CH_2FCF_3$. If desired, additional $CH_2FCF_3$ can be produced by reacting $CHF=CF_2$ with HF (see, e.g., U.K. Patent GB 2004539B). This invention further provides a process for the preparation of highly pure $CHClFCF_3$ from isomeric mixtures of $C_2HClF_4$, comprising contacting the isomer mixture with said zeolites to produce a product mixture which contains $CF_2=CF_2$ (and optionally perfluorocyclobutane) and $CHClFCF_3$.

In addition, the invention provides a process for producing perfluorocyclobutane by contacting $CHF_2CClF_2$ with said zeolite. Accordingly, a mixture of $C_2HClF_4$ isomer may be contacted with said zeolites to produce a product mixture which contains perfluorocyclobutane and $CHClFCF_3$.

Hydrochlorofluorocarbons which contain both fluorine and chlorine on the same carbon atom and hydrogen on the adjacent carbon atom can lose either fluorine or chlorine during the dehydrofluorination reaction. Typically, HCl is preferentially eliminated. However, some olefinic products are also produced by HF elimination.

The zeolites of Na—X (i.e., 13X) and Cs—Y which are considered useful for this invention are either commercially available or can be prepared by techniques well known in the art (e.g., cesium exchange with Na—Y).

The reaction temperature can be in the range of from about 100° C. to 500° C. provided that when $CHF_2CHF_2$ is hydrodefluorinated over Cs—Y, the reaction temperature is greater than 350° C. A preferred range for dehydrohalogenation reactions using 13X is from about 100° C. to about 300° C.

Pressure is not critical. Subatmospheric, atmospheric or superatmospheric pressures may be used. Inert gases such as nitrogen, helium and argon may be fed to the reactor along with the $C_2$ hydrochlorofluorocarbon and/or hydrofluorocarbon starting materials.

The hydrochlorofluorocarbon and/or hydrofluorocarbon starting materials of this invention are either commercially available or can be prepared by known methods.

The dehydrohalogenation reaction of this invention can be used in processes for the separation of isomeric mixtures of hydrochlorocarbons or hydrofluorocarbons. The dehydrohalogenation reaction is done under such conditions that one isomer is selectively converted to an olefin which can then be isolated and used for example, as a monomer for fluoropolymers. Alternatively, the olefin can be reacted with HF to afford the other isomer. The following are embodiments of this invention which illustrate its utility for the preparation of the indicated pure isomers.

The process based upon preferential $CHF_2CHF_2$ dehydrofluorination is particularly useful for purifying $CH_2FCF_3$ which contains minor amounts of $CHF_2CHF_2$. Where the process is used for such purification of $CH_2FCF_3$, the isomer mix to be purified by this process (i.e., the mix contacted with the zeolite) generally has a mole ratio of $CH_2FCF_3$ to $CH_2FCF_3$ of at least about 9:1, preferably at least about 19:1, and more preferably at least about 99:1. Contact with zeolites is preferably sufficient to reduce the mole ratio of $CHF_2CClF_2$ to $CH_2FCF_3$ by at least 25% compared to the mole ratio in the mix prior to purification (i.e., prior to contact with the zeolite), preferably by at least about 50%.

A mixture of the $C_2H_2F_4$ isomers may result, for example, from a process involving the reaction of $C_2Cl_2F_4$ isomers with hydrogen. Unreacted starting materials and $C_2HClF_4$ isomers may be recycled and reacted further with hydrogen to produce additional $C_2H_2F_4$. Additional impurities may be present in these products. Distillation is typically used in order to remove impurities such as HCl, HF, under- and over-chlorinates and fluorinates to produce products that are at least 90% $C_2H_2F_4$.

A mixture of $CHF_2CHF_2$ and $CH_2FCF_3$ containing at least 90% $CH_2FCF_3$ is contacted with a zeolite 13X at a temperature in the range of from about 100° C. to about 500° C. or with zeolite Cs—Y at a temperature in the range of from about 350° C. to about 500° C. $CHF_2CHF_2$ is preferentially dehydrohalogenated to $CHF=CF_2$. Some of the $CH_2FCF_3$ may also be dehydrohalogenated to $CHF=CF_2$. The olefin is separated from HFC-134a by conventional means such as distillation. The olefin can be used for the preparation of polymers or if desired it can be reacted with HF in a conventional manner to produce addtional HFC-134a. In this manner $CH_2FCF_3$ with an isomer purity of greater than 99.9% can be prepared.

In another embodiment of this invention, the process based upon preferential $CHF_2CClF_2$ dehydrofluorination is particularly useful for purifying $CHClFCF_3$ which contains minor amounts of $CHF_2CClF_2$. Where the process is used for such purification of $CHClFCF_3$, the isomer mix to be purified by this process (i.e., the mix contacted with the zeolite) generally has a mole ratio of $CHClFCF_3$ to $CHF_2CClF_2$ of at least about 9:1, preferably at least about 19:1, and more preferably at least about 99:1. Contact with the zeolites is preferably sufficient to reduce the mole ratio of $CHF_2CClF_2$ to $CHClFCF_3$ by at least 25% compared to the mole ratio in the mix prior to purification (i.e., prior to contact with the zeolite) preferably by at least about 50%.

A mixture of the $C_2HClF_4$ isomers may result, for example, from a process involving the reaction of $C_2Cl_4$ with hydrogen fluoride. Unreacted starting materials and under-fluorinated materials, e.g., $CHCl_2CF_3$ may be recycled and reacted further with hydrogen fluoride to produce additional $C_2HClF_4$. Additional impurities may be present in these products. Distillation is typically used in order to remove impurities such as HCl, HF, under- and over-chlorinates and fluorinates to produce products that are at least 90% $C_2HClF_4$.

A mixture of $CHF_2CClF_2$ and $CHClFCF_3$ containing at least 90% $CHClFCF_3$ is contacted with zeolite Cs—Y or with zeolite 13X at a temperature in the range of from about 100° C. to about 500° C., preferably, in the range of from about 100° C. to about 300° C. $CHF_2CClF_2$ is preferentially dehydrohalogenated to $CF_2=CF_2$, which can dimerize to form perfluorocyclobutane, especially at temperatures of less than 300° C. The olefin and/or its dimer are separated from $CHClFCF_3$ by conventional means such as distillation. In this manner $CHClFCF_3$ with an isomer purity of greater than 99.9 can be prepared.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication.

Without further elaboration, it is believed that one skilled in the art can, using the description herein, utilize the present invention to its fullest extent. The following specific embodiments are, therefore, to be construed as merely illustrative, and does not constrain the remainder of the disclosure in any way whatsoever.

EXAMPLE 1

A stainless steel metal tube 0.18 in. (4.6 mm) I.D.×4.5 in. (11.4 cm) was packed with zeolite 13X. The tube was mounted in a gas chromatography/mass spectrometer (GC/MS) unit. The column had been conditioned prior to these tests by heating to 200° C. under a nominal helium flow of 30 cc/minute. The packed columns used for these runs had been previously used for other runs involving halogenated hydrocarbons such as, $CF_3CF_3$, $CHF_3$, $CHClFCF_3$, $CHF_2CClF_2$, $CClF_2CF_3$, $CHF_2CF_3$, $CClF_2CClF_2$, $CCl_2FCF_3$, $CH_3CHF_2$, $CCl_2F_2$, $CHCl=CF_2$, $CH_3CF_3$, $CH_2FCHF_2$, $CH_3CHClF$, $CClF_3$, $CClF_2CF_3$, and $CH_2ClF$.

The gas chromatograph oven was set to the desired temperature. Helium flow was set at a nominal flow rate of 30 cc/minute using a flow meter. The actual helium flow was monitored as outgas on the system vacuum pump. Because the flow rate is only approximate, there was no attempt to alter the flow rate for each temperature run. The standard procedure for GC runs was to reset the flow rate to 30.0 cc/minute at each temperature. The gas was injected (25 µL sample) onto the column at each temperature and data were collected. When $CHF_2CHF_2$ was injected, only $CHF=CF_2$ was observed, no $CHF_2CHF_2$ was detected. The dehydrofluorination results are shown in Table 1 (elution times are in minutes).

TABLE 1

| Compound | Temp. (°C.) | Elution time F1123[a] | Abundance (peak height) | Elution time 134a | Abundance (peak height) |
|---|---|---|---|---|---|
| 134a[b] | 275 | 1.3 | 18000 | 5.5 | 2500 |
| | 250 | 2.2 | 9000 | 12.0 | 8000 |
| | 225 | 7.0 | 3500 | 26.0 | 10000 |
| | 200 | 20.0 | 2000 | 65.0 | 18000 |
| | 250 | 4.0 | 2500 | 12.0 | 3000 |
| 134[c] | 275 | 3.0 | 6000 | | |
| | 250 | 5.0 | 6500 | | |
| | 225 | 25.0 | 1000 | | |

TABLE 1-continued

| Compound | Temp. (°C.) | Elution time F1123[a] | Abundance (peak height) | Elution time 134a | Abundance (peak height) |
|---|---|---|---|---|---|

[a] 1123 is $CHF=CF_2$
[b] 134a is $CH_2FCF_3$
[c] 123 is $CHF_2CHF_2$

EXAMPLE 2

A stainless steel metal tube 0.18 in. (4.6 mm) I.D.×4.5 in. (11.4 cm) was packed with zeolite Cs—Y. The tube was mounted in a gas chromatography/mass spectrometer (GC/MS) unit. The column had been conditioned prior to these tests by heating to 200° C. under a nominal helium flow of 30 cc/minute. The packed columns used for these runs had been previously used for other runs involving halogenated hydrocarbons such as. $CF_3CF_3$, $CHF_3$, $CHClFCF_3$, $CHF_2CClF_2$, $CClF_2CF_3$, $CHF_2CF_3$, $CClF_2CClF_2$, $CCl_2FCF_3$, $CH_3CHF_2$, $CCl_2F_2$, $CHCl=CF_2$, $CH_3CF_3$, $CH_2FCHF_2$, $CH_3CHClF$, $CClF_3$, $CClF_2CF_3$, and $CH_2ClF$.

The procedure was the same as that used in Example 1. The dehydrohalogenation results are shown in Table 2.

TABLE 2

| Fluorocarbon | Temp. (°C.) | Eluted Products(elution time(min.)) |
|---|---|---|
| $CHF_2CClF_2$ | 150 | no peaks |
|  | 200 | C318*(19.4), *F124a[b](77.0) |
|  | 225 | C318(9.6), F114[c](29.4), *F124a(92.1) |
|  | 250 | *C318(5.7), F114(19.3) |
|  | 275 | *C318(3.6), F114(11.9), F124a(24.8) |
|  | 275 | TFE[d](1.1), *C318(3.1), F114(9.1), F124a(17.9) |
| $CHClFCF_3$ | 250 | CHClFCF_3(35.8) |
| $CHCl_2CHF_2$ | 275 | *F1122[e](7.9), F1121[f](29.8) |
| $CClF_2CHCl_2$ | 275 | *F1112a[g](4.6), F1111[h](15.0) |
| $CH_3CHF_2$ | 275 | *F1141[i](3.0) |
| $CHCl_2CF_3$ | 275 | *F1112a(7.9),F1111(22.5) |
| $CH_3CClF_2$ | 275 | *F1132a[j](1.3),F1131a[k](5.2) |

The asterisk symbol (*) designates the major peak eluted
[a] C318 is perfluorocyclobutane
[b] F124a is $CHF_2CClF_2$
[c] CF114 is $CClF_2CClF_2$
[d] TFE is $CF_2=CF_2$
[e] F1122 is $CHCl=CF_2$
[f] F1121 is $CHF=CCl_2$
[g] F1112a is $CCl_2=CF_2$
[h] F1111 is $CCl_2=CClF$
[i] F1141 is $CH_2=CHF$
[j] F1132a is $CH_2=CF_2$
[k] F1131a is $CH_2=CClF$

We claim:

1. A process for the purification of one isomer from a mixture of two isomers of partially halogenated ethanes of the formula $C_2H_aCl_bF_c$ where a is an integer from 1 to 4, b is an integer from 0 to 3 and c is an integer from 1 to 5, comprising:

contacting the mixture of $C_2H_aCl_bF_c$ isomers with a zeolite selected from the group consisting of NaX and CsY to selectively react the second isomer to produce an olefin selected from the group consisting of $C_2H_{a-1}Cl_{b-1}F_c$ and $C_2H_{a-1}Cl_bF_{c-1}$ by dehydrohalogenation.

2. The process of claim 1 wherein a mixture of $C_2H_2F_4$ isomers is contacted with said zeolite to produce a product mixture which contains $CHF=CF_2$ and $CH_2FCF_3$.

3. The process of claim 2 wherein the contact with said zeolite is sufficient to reduce the mole ratio of $CHF_2CHF_3$ to $CH_2CHF_2$ by at least 25%.

4. The process of claim 3 wherein the isomer mix contacted with the zeolite has a mole ratio of $CH_2FCF_3$ to $CHF_2CHF_2$ of at least about 9:1.

5. The process of claim 2 wherein the $CHF=CF_2$ is reacted with HF to produce additional $CH_2FCF_3$.

6. The process of claim 1 wherein a mixture of $C_2HClF_4$ isomers is contacted with said zeolite to produce a product mixture which contains $CF_2=CF_2$ and $CHClFCF_3$.

7. The process of claim 6 wherein the contact with said zeolite is sufficient to reduce the mole ratio of $CHF_2CClF_2$ to $CHClFCF_3$ by at least 25%.

8. The process of claim 7 wherein the isomer mix contacted with the zeolite has a mole ratio of $CHClFCF_3$ to $CHF_2CClF_2$ of at least about 9:1.

9. A process for producing perfluorocyclobutane, comprising:

contacting $CHF_2CClF_2$ with a zeolite selected from the group consisting of NaX and CsY.

10. A process for producing additional $CH_2FCF_3$ from a mixture of $CH_2FCF_3$ and $CHF_2CHF_2$, comprising:

contacting the mixture with a zeolite selected from the group consisting of NaX and CsY to selectively dehydrohalogenate the $CHF_2CHF_2$ to $CHF=CF_2$ and reduce the mole ratio of $CHF_2CHF_2$ to $CH_2FCF_3$ by at least 25%; and reacting the $CHF=CF_2$ with HF to product $CH_2FCF_3$.

11. The process of claim 10 wherein the mixture contacted with said zeolite has a mole ratio of $CH_2FCF_3$ to $CHF_2CHF_2$ of at least about 9:1.

* * * * *